US007003337B2

(12) United States Patent
Harjunmaa et al.

(10) Patent No.: US 7,003,337 B2
(45) Date of Patent: Feb. 21, 2006

(54) NON-INVASIVE SUBSTANCE CONCENTRATION MEASUREMENT USING AND OPTICAL BRIDGE

(75) Inventors: Hannu Harjunmaa, Holden, MA (US); Stevan Kun, Worcester, MA (US); Robert A. Peura, Princeton, MA (US); John A. Rolls, Armonk, NY (US)

(73) Assignee: VivaScan Corporation, West Boylston, MA (US)

( * ) Notice: Subject to any disclaimer, the term of this patent is extended or adjusted under 35 U.S.C. 154(b) by 0 days.

(21) Appl. No.: 10/134,310

(22) Filed: Apr. 26, 2002

(65) Prior Publication Data

US 2003/0204133 A1 Oct. 30, 2003

(51) Int. Cl.
*A61B 5/00* (2006.01)
(52) U.S. Cl. .................. 600/316; 600/322; 600/310
(58) Field of Classification Search ........ 600/322–326, 600/316, 334, 335
See application file for complete search history.

(56) References Cited

U.S. PATENT DOCUMENTS

| | | |
|---|---|---|
| 1,758,088 A | 5/1930 | Schmick |
| 2,721,942 A | 10/1955 | Friel et al. |
| 3,463,142 A | 8/1969 | Harte |
| 3,489,906 A | 1/1970 | Palle-Finn |
| 3,614,450 A | 10/1971 | Hill et al. |
| 3,638,640 A | 2/1972 | Shaw |
| 3,799,672 A | 3/1974 | Vurek |
| 3,926,527 A | 12/1975 | Pembrook et al. |
| 3,957,037 A * | 5/1976 | Fletcher et al. ............. 600/384 |
| 3,958,560 A | 5/1976 | March |
| 3,963,019 A | 6/1976 | Quandt |
| 4,029,085 A | 6/1977 | DeWitt et al. |
| 4,033,330 A | 7/1977 | Willis et al. |
| 4,169,676 A | 10/1979 | Kaiser |

(Continued)

FOREIGN PATENT DOCUMENTS

EP 0 074 428 B1 3/1983

(Continued)

OTHER PUBLICATIONS

Spanner, G., et al., "New Concept for the Non-Invasive Determination of Physiological Glucose Concentrations Using Modulated Laser Diodes", *Fresenius J. Anal. Chem* (1996) 354: 306-310.

(Continued)

*Primary Examiner*—Eric F. Winakur
(74) *Attorney, Agent, or Firm*—Hamilton, Brooks, Smith & Reynolds, P.C.

(57) ABSTRACT

An improved method for non-invasively measuring a concentration of a target analyte dissolved in a fluid flowing through a sample is presented. It includes directing a probe beam of electromagnetic radiation, consisting of time multiplexed components of different wavelengths, through the sample and measuring the difference of the absorption of the radiation at at least one wavelength pair at different sample states. During sample state changes, the amount of fluid containing the target analyte within the sample is changing, which varies the total amount of target analyte in the sample, as well as the absorption properties of the sample. The sample states are produced, for instance, by compressing and uncompressing the tissue sample. The accuracy of the presented method is enhanced by including continuous estimation of the amount of the fluid containing the target analyte within the sample, and measurement of the variations of the absorption at a wavelength at which the target analyte absorbs significantly. The method is particularly useful in measuring the concentration of a target analyte, such as glucose, in tissue containing blood. An apparatus for performing this method also is disclosed.

76 Claims, 2 Drawing Sheets

U.S. PATENT DOCUMENTS

| | | | |
|---|---|---|---|
| 4,266,554 | A | 5/1981 | Hamaguri |
| 4,267,844 | A | 5/1981 | Yamanishi |
| 4,306,877 | A | 12/1981 | Lubbers |
| 4,321,930 | A | 3/1982 | Jobsis et al. |
| 4,380,240 | A | 4/1983 | Jobsis et al. |
| 4,398,541 | A | 8/1983 | Pugliese |
| 4,427,889 | A | 1/1984 | Muller |
| 4,447,150 | A * | 5/1984 | Heinemann .................. 356/41 |
| 4,485,820 | A | 12/1984 | Flower |
| 4,490,845 | A | 12/1984 | Steinbruegge et al. |
| 4,513,751 | A | 4/1985 | Abe et al. |
| 4,523,279 | A | 6/1985 | Sperinde et al. |
| 4,570,638 | A | 2/1986 | Stoddart et al. |
| 4,586,513 | A | 5/1986 | Hamaguri |
| 4,603,700 | A | 8/1986 | Nichols et al. |
| 4,621,643 | A | 11/1986 | New, Jr. et al. |
| 4,641,658 | A | 2/1987 | Lepper |
| 4,653,498 | A | 3/1987 | New, Jr. et al. |
| 4,655,225 | A | 4/1987 | Dahne et al. |
| 4,694,833 | A | 9/1987 | Hamaguri |
| 4,704,029 | A | 11/1987 | Van Heuvelen |
| 4,714,080 | A | 12/1987 | Edgar, Jr. et al. |
| 4,725,147 | A | 2/1988 | Stoddart |
| 4,750,496 | A | 6/1988 | Reinhart et al. |
| 4,759,369 | A | 7/1988 | Taylor |
| 4,768,516 | A | 9/1988 | Stoddart et al. |
| 4,785,814 | A | 11/1988 | Kane |
| 4,796,636 | A | 1/1989 | Branstetter et al. |
| 4,805,623 | A | 2/1989 | Jobsis |
| 4,817,623 | A | 4/1989 | Stoddart et al. |
| 4,832,484 | A | 5/1989 | Aoyagi et al. |
| 4,854,699 | A | 8/1989 | Edgar, Jr. |
| 4,863,265 | A | 9/1989 | Flower et al. |
| 4,867,557 | A | 9/1989 | Takatani et al. |
| 4,882,492 | A * | 11/1989 | Schlager ..................... 600/322 |
| 4,883,055 | A | 11/1989 | Merrick |
| 4,907,594 | A | 3/1990 | Muz |
| 4,927,264 | A | 5/1990 | Shiga et al. |
| 4,975,581 | A | 12/1990 | Robinson et al. |
| 5,028,787 | A | 7/1991 | Rosenthal et al. |
| 5,054,487 | A | 10/1991 | Clarke |
| 5,099,123 | A | 3/1992 | Harjunmaa |
| 5,112,124 | A | 5/1992 | Harjunmaa et al. |
| 5,137,023 | A | 8/1992 | Mendelson et al. |
| 5,167,230 | A | 12/1992 | Chance |
| 5,178,142 | A * | 1/1993 | Harjunmaa et al. ......... 600/310 |
| 5,183,042 | A | 2/1993 | Harjunmaa et al. |
| 5,190,040 | A | 3/1993 | Aoyagi |
| 5,277,181 | A | 1/1994 | Mendelson et al. |
| 5,322,067 | A * | 6/1994 | Prater et al. ................. 600/443 |
| 5,372,135 | A * | 12/1994 | Mendelson et al. ......... 600/322 |
| 5,620,000 | A * | 4/1997 | Zinser et al. ................ 600/479 |
| 5,746,206 | A | 5/1998 | Mannheimer |
| 5,827,181 | A * | 10/1998 | Dias et al. ................... 600/322 |
| 6,151,516 | A * | 11/2000 | Kiani-Azarbayjany et al. .......................... 600/322 |
| 6,223,063 | B1 * | 4/2001 | Chaiken et al. ............. 600/310 |
| 6,285,894 | B1 | 9/2001 | Oppelt et al. |
| 6,292,686 | B1 * | 9/2001 | Chaiken et al. ............. 600/310 |
| 6,400,972 | B1 * | 6/2002 | Fine ........................... 600/322 |
| 6,615,061 | B1 * | 9/2003 | Khalil et al. ................. 600/310 |

FOREIGN PATENT DOCUMENTS

| | | |
|---|---|---|
| EP | 0 152 979 A1 | 8/1985 |
| EP | 0 226 822 A2 | 7/1987 |
| EP | 0 160 768 B1 | 5/1989 |
| EP | 0 404 562 B1 | 12/1990 |
| EP | 0 407 992 A1 | 1/1991 |
| EP | 0 997 103 A1 | 5/2000 |
| EP | 1 189 074 A2 | 3/2002 |
| WO | WO 90/04353 | 5/1990 |
| WO | WO 90/07905 | 7/1990 |
| WO | WO 91/15991 | 10/1991 |
| WO | WO 92/17765 | * 10/1992 |
| WO | WO 93/00855 | 1/1993 |
| WO | WO 98/43096 | 10/1998 |

OTHER PUBLICATIONS

Peura, R.A., et al., "Blood Glucose Sensors: An Overview", *IEEE/NSF Symposium on Biosensors*, 1984, pp. 63-68.

Heise, H.M. et al., "Multivariate Determination of Glucose in Whole Blood by Attenuated Total Reflection Infrared Spectroscopy", *Anal. Chem.* 1989, 61, 2009-2015.

Arnold, M., et al., "Determination of Physiological Levels of Glucose in an Aqueous Matrix with Digitally Filtered Fourier Transform Near-Infrared Spectra", *Anal. Chem.* 1990, 62, 1457-1464.

Marbach, R., et al., "Calibration Modeling by Partial Least-Squares and Principal Componenet Regression ant its Optimization Using an Improved Leverage Correction for Prediction Testing", *Chemometrics and Intelligent Labotatory Systems*, 9 (1990) 45-63.

Jansson, P., "Neural Networks: An Overview", *Analytical Chemistry*, vol. 63, No. 6, Mar. 15, 1991, pp. 357-362.

Donahoe, T. M., et al., "A New Noninvasive Backscattering Oximeter", *IEEE/Seventh Annual Conference of the Engineering on Medicine and Biology Society*, pp. 144-147, 1985.

* cited by examiner

NON-INVASIVE SUBSTANCE CONCENTRATION MEASUREMENT USING AND OPTICAL BRIDGE

BACKGROUND OF THE INVENTION

This invention relates to the non-invasive measurement of the concentration of substances that absorb electromagnetic radiation, such as light or infrared radiation, in absorbing and turbid matrices, such as human or animal body tissue, using a probe beam of electromagnetic radiation. The invention is particularly applicable to glucose measurement in human tissue using near-infrared radiation. It is, however, generally applicable to measurements of the concentration of any species that absorbs electromagnetic radiation, especially in strongly absorbing and turbid matrices.

The infrared measurement methods known in the art are not well adapted to the problem of quantifying an analyte, such as glucose, dissolved in a strongly absorbing solvent, such as blood. The known methods include separate or directly alternating measurements at a "glucose" wavelength and at a "reference" wavelength, where glucose does not absorb, as well as differential wavelength modulation about a glucose absorption band (C. Dähne, D. Gross, European patent 0 160 768 and references therein). In the known methods, the signal is easily masked with the variations of the strong background presented by water and other constituents in the tissue and in the capillary blood flow.

The present invention is an improvement over U.S. Pat. No. 5,099,123, issued to Harjunmaa (hereafter, the "'123 patent"), which is incorporated herein in its entirety by reference. The balanced differential (or "optical bridge") method disclosed in the '123 patent utilizes two wavelengths for target analyte concentration measurements. The first, or principal wavelength is chosen such to be highly absorbed in the target analyte. The second, or reference wavelength is chosen using a balancing process so that both wavelengths have substantially identical extinction coefficients in the background matrix. A radiation beam is generated that contains these two wavelengths in alternate succession at a suitable frequency. When the beam is properly balanced for the measurement, a sample detector, placed to measure radiation transmitted or reflected by the sample matrix that contains only a residual amount of the target analyte, will detect only a very small alternating component in the radiation, regardless of the thickness of the sample. When there is a relatively substantial amount of the target analyte in the sample matrix, however, the detector will detect a significant alternating signal synchronous with the wavelength alternation. This alternating signal is amplified and is then detected using a phase-sensitive detector (or lock-in amplifier). The optical bridge balancing process entails nulling out the alternating signal from the sample detector by systematically varying the relative intensities and/or wavelengths of the repetitive radiation periods. An auxiliary detector is also used to sample the combined beam before it enters the tissue in order to enhance the measurement stability. Although suitable for the purposes intended, the realization of the precautions taken to deal with the unavoidable differences in the spectral response between the auxiliary detector and the sample detector make the system somewhat complicated.

Subsequently in U.S. Pat. No. 5,178,142, (hereafter, the "'142 patent"), which is also incorporated by reference herein in its entirety, Harjunmaa et al. disclosed an improved method and apparatus in which the concentration measurement is performed using a two-wavelength alternating radiation probe beam which interacts with the tissue. One of the wavelengths is used as a reference wavelength, and the other is the principal wavelength. The reference wavelength is tunable to account for the expected variability of the background spectrum. After passing through the matrix that contains a given reference concentration of analyte, detected signals from the probe beam are balanced or nulled by tuning the variable wavelength beam over a range of frequencies. Next, the blood content of the sample is changed. The alternating component of the interacted probe beam is then detected. The amplitude of the alternating component of the signal given by the sample detector is proportional to the concentration of analyte or the difference from a preset reference analyte concentration.

Other related patents include U.S. Pat. Nos. 5,112,124; 5,137,023; 5,183,042; 5,277,181 and 5,372,135, each of which is incorporated by reference herein in its entirety.

SUMMARY OF THE INVENTION

This invention relates to systems and methods for non-invasively estimating the concentration of a target analyte in a sample. For the purpose of simplicity, and to aid in the understanding of the principles of this invention, the sample is defined as consisting of three components: non-fluid, bound fluid, and unbound fluid. The non-fluid and bound fluid components are generally fixed, and together are referred to as the background matrix. In the case of human tissue, for example, the background matrix comprises the cellular matrix and intra-cellular fluid. The third main component, the unbound fluid, is generally not fixed in the sample, and can freely circulate through the fixed background matrix of the sample. In human tissue, for instance, the unbound fluid consists of blood and other substances dissolved in or otherwise contained within the blood. The unbound fluid can be displaced by, for instance, compressing (squeezing) the sample. Also, in human tissue, the interstitial fluid can be considered to be bound fluid if the sample compression lasts for less than 20–30 seconds.

If not specified otherwise, the term "fluid" as used herein refers to the unbound fluid only. Generally, according to the present invention, the concentration of the target analyte in the unbound fluid is different from the concentration of the target analyte in the background matrix.

The present invention relates to a series of improvements to the known balanced differential, or "optical bridge," systems for measuring the concentration of a target analyte in a sample. As used herein, "optical bridge" refers to an apparatus and/or method for quasi-simultaneous differential optical measurement of very small absorbance differences of a sample, performed at one or more wavelength pairs. According to one aspect, the improved optical bridge method and system of present invention includes: 1) time-series measurements during and after a sample thickness variation; 2) synchronization of the measurements with the unbound fluid (e.g. blood) inrush into the sample; and, 3) the use of parameters extracted from the time-series measurements to compensate for daily and long-term variations in the absorption of the sample background matrix. An advantage of the present invention is the ability to record signals from a sample whose composition varies with time, while maintaining the sample at a substantially constant thickness, thus removing the thickness change as a major contributor to the signal. Accordingly, a simpler measurement system is provided which is capable of improved accuracy of target analyte concentration estimation.

An apparatus according to this invention includes a source for producing a beam of electromagnetic radiation. This beam consists of time multiplexed components (principal and reference) of desired narrow line-width wavelengths, and is produced, for instance, using a tunable filter. In alternative embodiments, two or more separate substantially monochromatic sources, whose outputs are combined into a single beam, can also be employed.

During a measurement, the alternating-wavelength probe beam passes through (or is reflected from) a sample mounted in a compression device. The compression device controllably varies the thickness of the sample (and consequently its unbound fluid content) during the measurement. A sample detector is positioned to receive the probe beam after it passes through the sample. The sample detector then feeds a signal to an analog signal pre-processing module that includes the hardware implementation of the optical bridge. The output optical bridge signal is then fed to a processor, which is programmed to calculate the target analyte concentration in the unbound fluid, based on parameters extracted from the sample detector signal and other auxiliary variables and time-varying signals.

One of the auxiliary signals used in the calculation of the target analyte concentration is preferably a time-varying estimate of the unbound fluid (e.g. blood) content within the sample. This estimate can be obtained, for example, by a separate, auxiliary blood signal detector measuring the sample transmission (or reflection) of light from a separate light source that provides radiation distinct from the wavelengths used for the target analyte measurement, preferably at a wavelength where hemoglobin absorbs, and even more particularly at a wavelength where hemoglobin absorption is independent of its oxidation state (i.e., isosbestic point). In other embodiments, a laser Doppler flow meter may be used to obtain a measurement of sample blood content.

Preferably, the movement of the compression device is synchronized with the unbound fluid inrush into the sample. In case of glucose measurement in the blood, the synchronization can be achieved using a separate, auxiliary synchronization detector measuring the sample transmission (or reflection) of light from a separate light source that provides radiation distinct from the wavelengths used for the target analyte measurement, and preferably at a wavelength where hemoglobin absorbs. The synchronization can also be achieved using a pulse oximeter.

Additional enhancements to the target analyte measurement can be achieved by measuring the temperature of the sample and/or the temperature of the detectors, and incorporating these variables into the processing of the detector output.

A method, according to this invention, for non-invasively measuring a concentration of a target substance (e.g., glucose) in a matrix (e.g., tissue) includes the following steps. First, the sample is compressed by the compression device to force out the unbound fluid that contains the majority of the target analyte. The sample is then illuminated with the probe beam of electromagnetic radiation. Preferably, the beam includes a principal period and a reference period, wherein during the principal period the effective wavelength of the radiation is more strongly absorbed by a target analyte, such as glucose, than is the effective wavelength of the radiation during the reference period. By way of illustration, the wavelength that is strongly absorbed by glucose can be between approximately 1550 and 1700 nm, and the wavelength lightly absorbed by glucose can be between approximately 1350 and 1430 nm.

In one embodiment, both the principal and the reference wavelengths are universally pre-set, or pre-set individually for each patient. In another embodiment, the reference and/or principal wavelengths are selected during a balancing process. This balancing process can be performed prior to measurement. The balancing process comprises, for example, tuning the wavelength and/or intensity of at least one of the alternating radiation periods to obtain a substantially-zero alternating component of the sample detector signal (i.e. the optical bridge signal) at chosen sample thicknesses/pressures exerted by the sample compression device. The optical bridge is "balanced" when there is substantially no alternating component in the signal generated by the sample detector. A properly balanced optical bridge means that the principal and reference wavelengths are equally absorbed by the sample matrix, which contains only residual amounts of the target analyte.

A measurement sequence comprises a series of individual measurements of intensities of the transmitted/reflected probe beam wavelength components obtained by the sample and auxiliary detector(s). This series of measurements is obtained during an alteration of sample thickness, and also over the subsequent sample content equilibration process that follows the alteration of sample thickness. The measurements are preferably obtained while the unbound fluid content of the sample is changing.

In a preferred embodiment of the invention, the sample thickness change is synchronized with the heartbeat. One advantage of this is that since the influx speed of blood depends on the blood pressure, performing the uncompression at a constant phase of the cardiac cycle produces blood refill time profiles that are substantially constant in shape. The cardiac phase can be chosen so as to also provide the fastest possible blood content change.

Measurements of auxiliary parameters (including, for example, unbound fluid content, temperature of sample and detector, sample thickness, and/or electronic control system operational parameters) accompany the measurements of the probe beam intensities. The recorded data is further combined with corresponding estimates of the time-varying unbound fluid content over the same time. An algorithm, based on modeling, is used to extract characteristic parameters from the time-series profiles, and combines these parameters with other measured parameters to achieve improved specificity and sensitivity in the estimation of the target substance concentration.

Using the method of the present invention, the accuracy of the target analyte measurement is improved by isolating and quantifying the component of the optical bridge signal that results from the presence of the analyte rather than other "parasitic" factors. More specifically, where the targeted analyte is located primarily within the unbound fluid rather than the fixed structure of the matrix, the magnitude of the optical bridge signal depends directly on the amount of fluid within the sample. Thus, if the varying unbound fluid content of the sample is estimated and plotted against the magnitude of the optical bridge signal over time, the result is a substantially straight line whose slope is directly related to the concentration of analyte in the sample, assuming that the other factors contributing to the "parasitic" signal, including shifts in the effective wavelength due to changes in sample thickness, remain relatively constant during the measurement process.

BRIEF DESCRIPTION OF THE DRAWINGS

The foregoing and other objects, features and advantages of the invention will be apparent from the following, more particular description of preferred embodiments of the invention, as illustrated in the accompanying figures. The drawings are not necessarily to scale, emphasis instead is placed on illustrating the principles of the invention.

DETAILED DESCRIPTION OF THE INVENTION

The features and other details of the method of the invention will now be more particularly described with reference to the accompanying drawings and pointed out in the claims. It will be understood that the particular embodiments of the invention are shown by way of illustration and not as limitations of the invention. The principal features of this invention can be employed in various embodiments without departing from the scope of the invention.

One embodiment of an apparatus for performing a method of the invention to measure glucose concentration in blood based on transmitted light through the sample will now be explained in detail in connection with FIG. 1. A similar apparatus may be designed which uses reflected light instead of transmitted light.

The light source 10 is preferably a quartz-halogen lamp powered by power supply 20. Using optical elements 21, the lamp light is directed to an optical tunable filter 30. The characteristics (wavelengths, intensities and duration of each wavelength component) of the probe beam (output 202 from the optical tunable filter 30) are controlled by filter driver 111. In performing the methods of this invention, an acousto-optical tunable filter has been used.

In an alternate embodiment, a pair of tunable monochromatic light sources, such as tunable laser diodes, may be used to produce the probe beam 202.

Clock generator 110 produces a timing signal at the desired chopping frequency $f_{ch}$ needed for time multiplexing of the principal and reference components of the probe beam. The CPU 104 generates signals for controlling the principal intensity $I_P$, both wavelengths $\lambda_P$ and $\lambda_R$, and the chopping frequency $f_{ch}$ of the probe beam 202.

The probe beam 202 exiting from optical filter 30 is directed, using optical elements 40, to beam splitter 50, from which a fraction 208 of probe beam 202 is directed to auxiliary detector 60. The auxiliary detector 60 is connected to a PID (proportional—integral—derivative) controller 102 that extracts the intensity difference between the two components (principal and reference) of the detected beam, compares that difference voltage with a pre-set voltage, and by means of controlling the intensity of the reference wavelength component $I_R$ 314, maintains the difference of the two wavelength intensities constant. An alternative embodiment maintains the ratio of the two wavelength intensities constant. These features make the system stable against changes in light source output caused by, for instance, aging of the lamp or other components, or from light source power variations.

The majority of the probe beam is directed onto diffuser plate 70. Placing a diffuser plate in the beam path before the sample provides the advantage of minimizing the effects of the variation in the scattering properties of the sample. The sample specimen 80, such as an earlobe, lip, cheek, nasal septum, tongue, or the skin between the fingers or toes of the subject, is placed between diffuser plate 70 and sample detector lens 92, and is compressed by moving the measurement head 90, mounted on compression mechanism 400. The probe beam 203 transmitted through sample 80 is focused by sample detector lens 92, and directed to dichroic mirror 93. The major portion of the probe beam is transmitted by dichroic mirror 93 to sample detector 91. The sample detector 91 detects the intensity at each of the wavelength periods of the probe beam 205 transmitted through sample 80, and sends an electrical signal 302 to preamplifier 26 and phase sensitive detector (or lock-in amplifier) 24. The output signal 308 from the phase sensitive detector 24 is proportional to the difference (or ratio) of the principal and reference intensities detected by sample detector 91. This signal 308 is referred to as the optical bridge signal.

Figure 1:
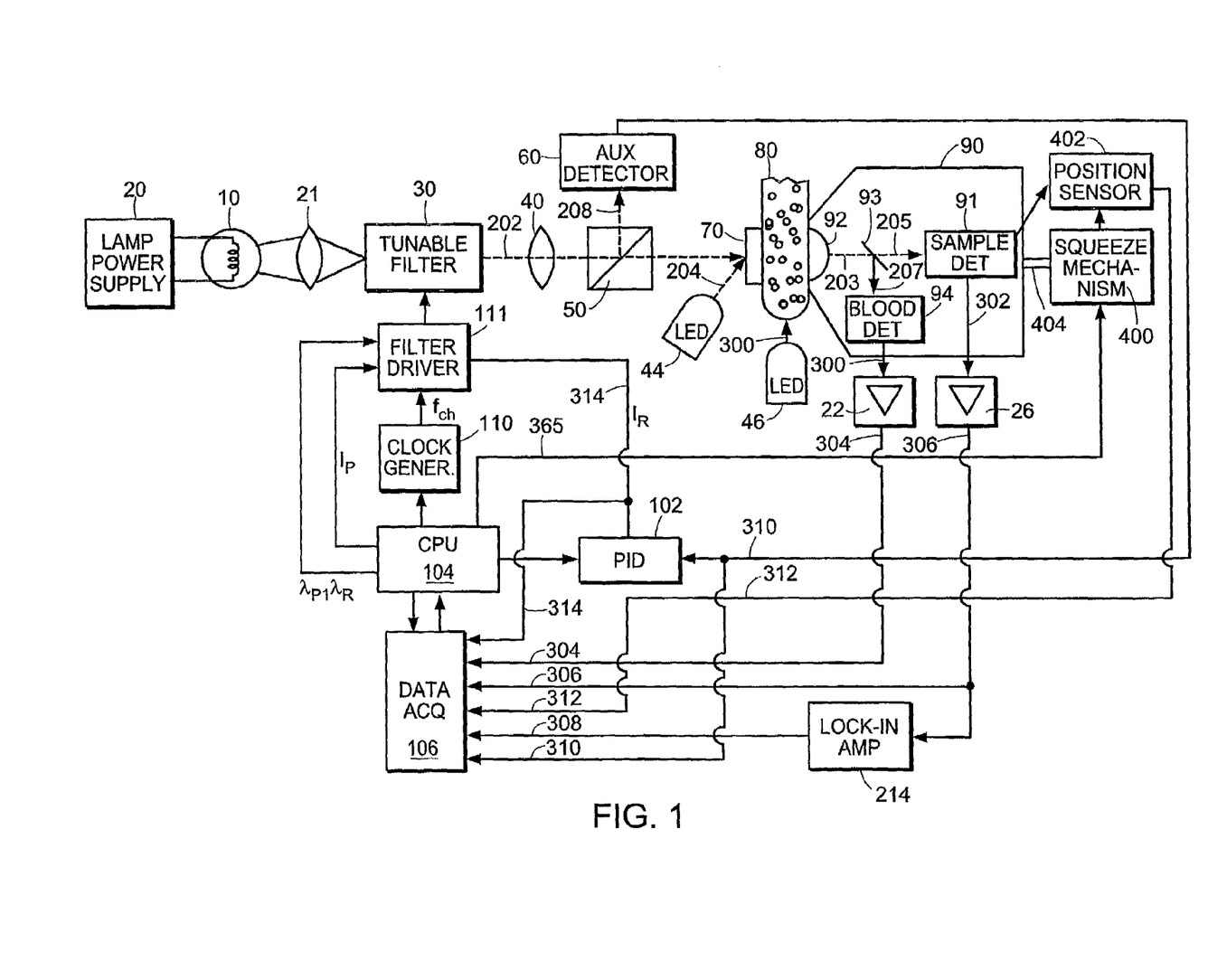
FIG. 1 is a schematic block diagram of an apparatus of the invention.

In this embodiment, also shown in FIG. 1, a separate auxiliary radiation source such as an infrared or visible-light LED 44, is used to provide an estimate of the sample blood content. This auxiliary radiation source 44 produces a blood detection beam 204 that is directed onto the diffuser plate 70 and into the sample. An LED operating at a wavelength of, for instance 525 nm (an isosbestic wavelength for hemoglobin), provides a good sensitivity to blood. The sample detector 91 can be used to detect the transmitted portion of the blood detection beam 204. However, since there is a significant ambient light in this wavelength range, it is advantageous to use a separate blood signal detector 94 to detect the blood detection beam 204. To achieve this, the transmitted blood detection beam is reflected by the dichroic mirror 93 to the blood signal detector 94, producing a blood signal 300. The blood signal 300 is then sent to the blood signal processing preamplifier 22. The dichroic mirror 93 in this embodiment also eliminates ambient light from the sample detector 91 by transmitting only infrared wavelengths.

In accordance with another embodiment, the blood content is estimated using a laser Doppler flowmeter integrated into the system, with a needle probe mounted on the optical axis. The laser Doppler flowmeter measures the number of moving red blood cells in its field of view, which extends to about 1 mm into the tissue. While the needle probe may block some light from the central portion of the optical bridge beam, the loss of light is tolerable. While the optical bridge measurements are performed, the laser Doppler instrument simultaneously takes its own readings of blood circulation under the skin. Accordingly, an estimate of the amount of blood in the measurement field at the time of measurement is provided.

Other possible techniques for obtaining an estimate of the blood content include ultrasound and electrical impedance plethysmography.

In the embodiment shown in FIG. 1, the pulse detection for synchronizing the measurements with the unbound fluid (e.g. blood) inrush into the sample is accomplished using an additional radiation source, similar to auxiliary radiation source 44. This, radiation source 46, can also be a LED operating at a wavelength of, for instance 525 nm, an oxyhemoglobin isobestic point. This radiation source 46 should be directed at a portion of the sample that at all times maintains good circulation, such as a section of the sample that is not compressed by the measurement head. The radiation source 46 generates a pulse detection beam 206 that is aimed at the sample 80. This beam is scattered by the tissue, and a fraction of the original beam 206 is collected by sample detector lens 92, is reflected by dichroic mirror 93, and is detected by blood signal detector 94.

Preferably, the two auxiliary radiation sources 44 and 46 are not operated at the same time. The pulse synchronization source 46 should be operated prior to the measurement step in order to synchronize the start of the measurement process with a variation of the unbound fluid (e.g. blood) pressure. The blood detection source 44 should be operated during the measurement process to provide a time-varying estimate of the unbound fluid content within the sample. The intensities of the two auxiliary radiation beams 204 and 206 are pre-set or can be controlled by the CPU 104.

To perform a measurement, the sample 80 is introduced between diffuser plate 70 and sample detector lens 92. The measurement head 90 is moved by compression mechanism 400 to gently compress sample 80 until a predetermined pressure is exerted on sample 80. The preferred embodiment of compression mechanism 400 includes a miniature linear actuator. Its step size, speed and travel distance are controlled by the CPU 104. Although this embodiment uses an electrical actuator, a hydraulic or a pneumatic actuator could also be used, with the ensuing advantages of compactness of the compression mechanism. A position sensor 402 is used to monitor the effects of the motor movement.

In this description, three different types of probe beam attenuations are distinguished. First is the background matrix, the second is the target analyte, while the third is the unbound fluid attenuation.

The background matrix attenuation results from the absorption of probe beam 202 by sample constituents whose concentrations are substantially constant throughout fixed sample compartments. The target analyte attenuation is caused by absorption of probe beam 202 by the target analyte (e.g. glucose), which is mostly concentrated in the unbound fluid (e.g. blood). When the tissue is sufficiently compressed, the unbound fluid, along with the target analyte (e.g. glucose), is substantially displaced from the sample 80. Since the concentration of the target analyte in the unbound fluid is different than its concentration in the background matrix (e.g. intracellular concentration), its average concentration in the beam path changes as a result of the compression. This concentration change allows the target analyte to be detected by this method.

The principal wavelength $\lambda_P$ of probe beam 202 is selected in such a way to have high attenuation by the target analyte. The principal wavelength intensity $I_P$ is set to achieve an optimal transmitted signal intensity. The reference wavelength $\lambda_R$ of the probe beam is either pre-set or selected during the optical bridge balancing process. Its intensity $I_R$ should be adjusted before each measurement as explained below in the description of the measurement process.

In the following text, a simple to understand example of a bridge balancing process is presented. It will be readily understood by those skilled in the art that different, more complex, bridge balancing procedures can also be used, with corresponding variations of the signal processing algorithm.

In the first step of bridge balancing, sample 80 is sufficiently compressed to remove the major amount of unbound fluid from the sample tissue. The principal wavelength parameters $\lambda_P$ and $I_P$ are set, and the reference wavelength $\lambda_R$ is initialized. The probe beam 202 is directed at the sample, and the optical bridge is balanced or nulled by adjusting the intensity of the probe beam reference wavelength intensity $I_R$ to obtain a substantially-zero optical bridge signal 308. In other embodiments, the reference wavelength intensity $I_R$ is set, while the principal wavelength intensity $I_P$ is adjusted to balance the bridge. Next, the sample compression pressure is released by a predetermined amount, called "step 1 incremental thickness" (typically 0.1 mm) and the probe beam reference wavelength $\lambda_R$ is adjusted by a signal from CPU 104 so as to again achieve a substantially-zero optical bridge signal 308. The initial compression pressure is chosen such that, even after releasing sample 80 by the step 1 incremental thickness, there is nearly no unbound fluid reflow into the sample. Changes in the optical bridge signal 308, due to this thickness increase result merely from increased background matrix thickness and not from any influx of fluid. Sample 80 is then compressed again back to its original compressed thickness, and the intensity at the reference (or principal) wavelength is again adjusted by the CPU 104 to achieve minimum optical bridge signal.

This two-thickness procedure may be repeated until a substantially-zero optical bridge signal is obtained at both thicknesses. At this point, the absorption coefficient of sample 80 in its compressed state is substantially equal at the two wavelengths $\lambda_P$ and $\lambda_R$. Although the reference wavelength can be balanced to completely zero the optical bridge signal, a non-zero signal must generally be contended with in practice. During the measurement process, this non-zero optical bridge signal can be subtracted from detector outputs to improve the accuracy of the measurement.

In one embodiment, the balancing is limited to only one cycle in order to speed up the measurement and reduce the compression stress on the sample.

Due to the monochromatic components of the probe beam, and a completely diffused light field, the sample constituents that have substantially constant concentrations throughout fixed sample compartments do not give rise to any optical bridge signal, irrespective of their absorbance spectra. This holds true even for constituent substances that have differential absorbance across the wavelength pair. Accordingly, these constituents do not interfere with an optical bridge measurement, regardless of the sample thickness.

This completes the optical bridge balancing phase; at this point both wavelengths and their intensities have been established. The instrument is ready to perform a measurement. A typical sequence for measurement of glucose in blood will be described in the following text, with reference to the measurement apparatus of FIG. 1, and the processing steps shown in FIG. 2. It will be understood that, in accordance with at least one embodiment of the invention, all blocks, signals, and paths shown in FIG. 2 reside within CPU 104.

Figure 2:
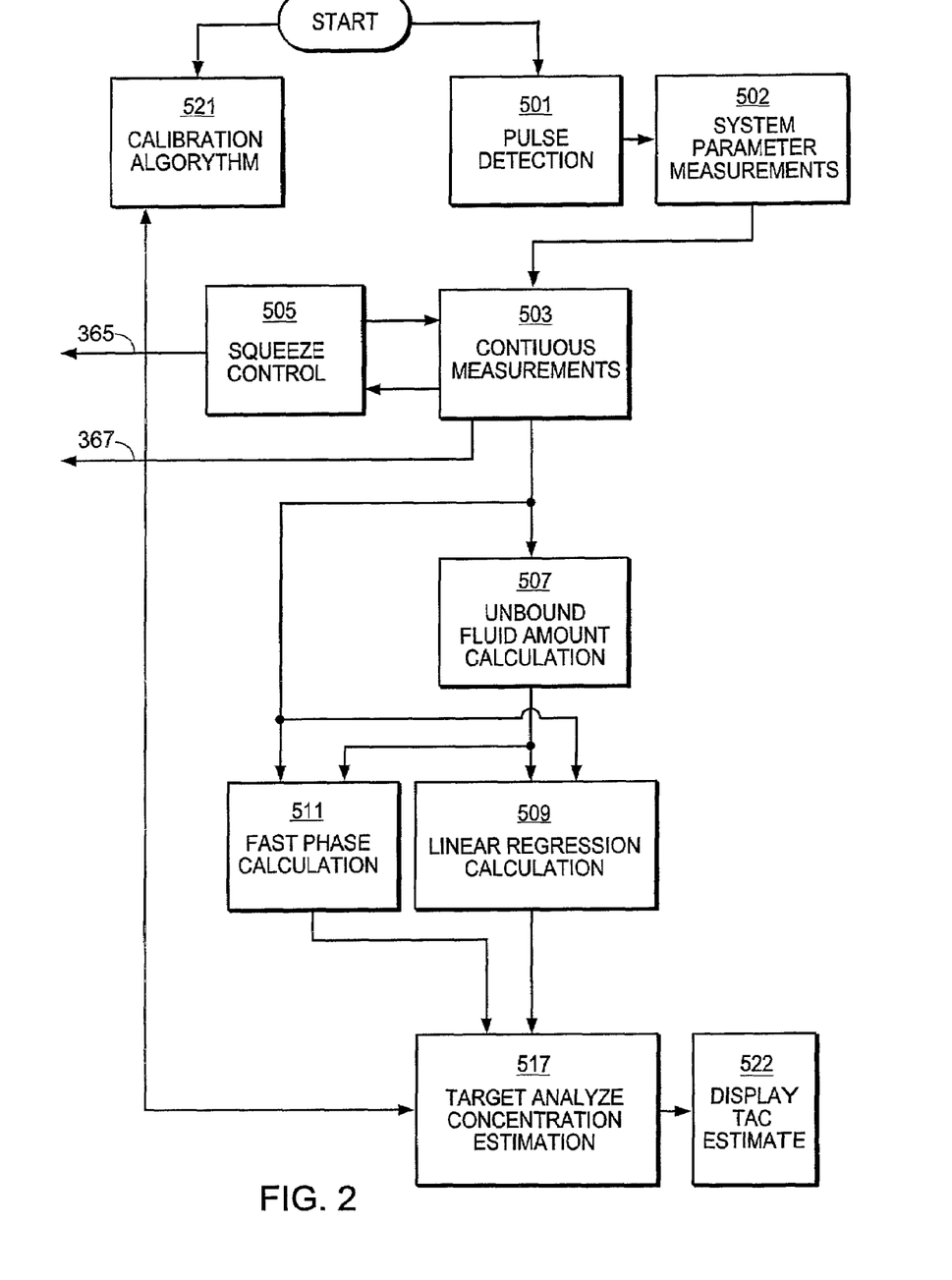
FIG. 2 is a block diagram schematically illustrating an embodiment of the components and steps for processing the time-varying detector signals and other measured parameters to obtain an estimate of analyte concentration, in accordance with one aspect of the invention.

With the probe beam still directed through the fully compressed sample, pulse-detection LED 46 is turned on, the measurement of blood signal 304 from blood signal detector 94 starts, and a pulse detection subroutine 501 (FIG. 2) is performed using a real-time analysis of the digitized blood signal 304. Pulse detection subroutine 501 recognizes systolic and diastolic phases of blood signal 304. After the subroutine 501 locks onto the pulse of the sample, the CPU 104 turns off pulse LED 46 and turns on blood detection LED 44. The CPU 104 then waits for a period determined by subroutine 501, and generates a trigger signal to start the measurements synchronized with the heart beat phase. First, a set of system parameter measurements is performed, as instructed by subroutine 502 (FIG. 2). As shown in FIG. 1, a plurality of system parameter signals are generated, which can be sent to data acquisition unit 106 that is in communication with CPU 104. Examples of these system parameter measurement signals include residual optical bridge value 308, principal and reference wavelength intensities measured by the sample and auxiliary detectors (306 and 310, respectively), and PID and position sensor values (314 and 312, respectively). The sample and detector temperatures can also be measured and recorded.

Generally, the sample 80 is maintained in the compressed state to displace the unbound fluid content for a time period of approximately 1 to 100 seconds.

Next, continuous measurements of the time-varying signals begin, including time-varying measurements of the optical bridge output 308, blood signal 304, and position sensor output 312.

Once these measurements begin, the compression mechanism 400 then starts opening the measurement head 90 by an amount and rate set by the CPU 104. According to one aspect, the head opening may have an initial fast phase, followed by a secondary slow phase. The amount of head opening may be fixed (e.g. 0.5 mm for a human ear), or may be thickness dependent (e.g. 30% of the compressed sample thickness). It is directly controlled from the subroutine for compression control 505, via connection 365. The purpose for the fast opening phase is to allow the unbound fluid that contains the target analyte to return into the sample. The optional slow phase head opening is designed to compensate for the background matrix thickness displacement resulting from the fluid influx and is also controlled by compression control subroutine 505.

The opening of the compression mechanism causes a change in the sample composition, which makes the sample absorb differently at the two wavelengths. This change in absorption of the two wavelengths results in a non-zero optical bridge signal 308. The measurements continue until stopped by CPU 104. Typically, the time-varying signal series should contain several hundred data sets, which are recorded over a measurement time period of approximately 0.1 to 10 seconds after the sample uncompression begins.

This concludes the measurement process, which is then followed by signal processing. An example of the steps for processing the time-varying detector signals and other measured parameters and calculating an estimate of the concentration of the target analyte is illustrated schematically in FIG. 2.

The optical bridge signal can be represented with the following simplified equation:

$$OBS = CCS \cdot UFA \cdot TAC + CCI \qquad (Eq. 1)$$

where:
OBS=optical bridge signal,
CCS=calibration constant slope,
UFA=unbound fluid amount,
TAC=target analyte concentration,
CCI=calibration constant intercept, and
TAA=target analyte amount=UFA·TAC.

In the case where the optical bridge has been ideally balanced for a measurement, the magnitude of the measured optical bridge signal, OBS (see Eq. 1), represents the difference in the absorbed light intensity at the two wavelengths resulting from the absorption of the target analyte within sample 80. This difference is proportional to the difference of the absorption by the target analyte at the two wavelengths, as well as to the amount of the target analyte in the sample. The amount of target analyte in the unbound fluid of the sample can be calculated as the product of the unbound fluid amount, UFA, and the target analyte concentration, TAC, in the unbound fluid. The difference of the absorption by the target analyte at the two wavelengths is known (CCS and CCI in Eq. 1), and is determined during a calibration process described in greater detail below. In order to obtain the concentration of the target analyte TAC (e.g. glucose) in the unbound fluid (e.g. blood), the optical bridge signal, OBS 308, is normalized with the amount of the unbound fluid, UFA.

As shown in FIG. 2, the unbound fluid amount, UFA, is calculated using subroutine 507. This calculation is based upon the fact that the time-series recording of the transmitted principal wavelength intensity signal 306 is dependent on the variation of the total amount of fluid in the optical path. This dependence is non-linear and relative. Similarly, the time-series recording of the blood signal 304 is dependent on the variation of the amount of unbound fluid in the optical path, and this dependence is also non-linear and relative. Subroutine 507 can thus perform mathematical modeling and self-normalization using time-series recordings 304 and 306 to calculate an estimate the time-varying amount of the unbound fluid, UFA.

Theoretically, once the system is calibrated, and the unbound fluid amount is calculated, the target analyte concentration can be calculated directly from Equation 1 using the calibration constants, CCS and CCI, and the instantaneous values of the optical bridge signal, OBS, and the unbound fluid amount, UFA. Due to physiological noise (variations of sample's physiological properties within the measurement interval), however, measurement enhancements should generally be performed to increase the accuracy of the target analyte concentration estimation. For this reason, multiple (preferably several hundred) measurements of the time-varying signals are obtained during and after the sample thickness alteration. These measurements are then processed using calculation subroutine 509.

In accordance with at least one embodiment of the invention, calculation subroutine 509 performs a linear regression of the optical bridge time-series measurements (OBS) vs. the calculated unbound fluid amount (UFA) time-series, over a time window beginning after the end of the fast phase of the opening of measurement head 90. The slope of the regression line is the parameter that is, in principle, directly correlated to the target analyte concentration. In principle, this slope is also independent of the amount of unbound fluid entering the sampling area, and also independent of the speed at which the unbound fluid enters the sampling area.

As the unbound fluid enters the sample volume, it displaces some of the non-fluid and bound fluid. This displacement can affect the accuracy of the optical bridge signal in a predictable manner. Subroutine 511 is designed to cancel this effect by using a fast phase correction that is calculated from the change to the signal during the opening (i.e. fast phase) movement of the measurement head.

Subroutine 517 then calculates an estimate of the target analyte concentration (TAC) in the unbound fluid using the measured system parameters and the previously-described parameters calculated by subroutines 507 (UFA) and 509 (regression), in combination with the calibration coefficients, CCS and CCI, determined by calibration algorithm 521. The target analyte concentration (TAC) value is calculated based upon the relationship described in Equation 1, and this value may be displayed, digitally or otherwise, at step 522.

The measurement system is calibrated prior to performing predictive estimations of the target analyte concentration. The calibration constants, CCS and CCI, are determined by calibration algorithm 521. The calibration algorithm 521 performs the previously-described measurement process, except that during the calibration process, the concentration of the target analyte is a known quantity. Preferably, at least two and typically between 4 and 10 measurement sequences are performed on samples with varying and known concentrations of the target analyte. The measurement sequence for calibration is identical to the one used in predictive estimation, except that at the end of the procedure, the calibration constant(s), rather than the analyte concentration, are calculated and stored for future reference. Using the relationship of Equation 1, the calibration algorithm 521 calculates the calibration constant(s) by performing best fit regression between the known concentrations of the target analyte and the above-described calculated parameters determined by subroutine 517, and determines the calibration constants from the regression. Typically, there is one multiplication calibration constant, CCS, and another additive constant, CCI. These calibration constants are later used by subroutine 517 to calculate the target analyte concentration (TAC) in a predictive measurement where the analyte concentration is unknown.

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention.

For example, while the method is here described as applied to an optical bridge employing an acousto-optical tunable filter, it can also be applied to different implementations of the optical bridge, such as one equipped with tunable diode lasers or other means to generate a beam containing the required wavelength pairs. Moreover, although the method is here described with a focus toward measuring the concentration of glucose in blood, the method and apparatus of this invention may also be employed to detect the concentration of other analytes such as cholesterol, urea, heavy metals, alcohol, nicotine or drugs in blood or other fluids. Further, sinusoidal, rather than square, modulation waveforms that are set 180° out of phase and result in a substantially constant total intensity, can alternatively be used to form the combined radiation beam. Also, measurements of radiation reflected by the tissue, rather than transmitted radiation, can be performed to obtain the desired data.

Accordingly, the foregoing description is by way of example only, and not limiting. The invention is limited only as defined in the following claims and equivalents thereto.

What is claimed is:

1. A method of non-invasive measurement of a concentration of a target analyte in a fluid within a sample matrix, the method comprising the steps of:
    directing a combined beam of electromagnetic radiation at the sample, the combined beam including at least two repetitive periods of radiation having different wavelengths, the target analyte having different absorption coefficients for two of the different wavelengths, the two wavelengths forming a wavelength pair;
    while the sample is at a first sample fluid state having an initial amount of fluid, detecting the combined beam with a sample detector arranged to detect a portion of the radiation transmitted through or reflected by the sample to generate an output signal proportional to the intensity of the combined beam at each of the two repetitive periods of radiation of the wavelength pair;
    subjecting the sample to a second sample fluid state to change the amount of fluid within the sample;
    measuring the output signal of the sample detector and obtaining an estimate of the amount of fluid in the sample while the amount of fluid in the sample varies from the initial amount in the first fluid state to a second amount in the second fluid state; and
    combining the measured output signal from the sample detector with the estimate of the amount of the fluid containing the target analyte to produce an estimate of the concentration of the analyte in the fluid; wherein during one of the sample fluid states, the detected intensities at each of the at least two repetitive periods of radiation are made substantially equal by adjusting the intensity of at least one of the repetitive periods of radiation entering the sample.

2. The method of claim 1, wherein one of the sample fluid states is chosen to displace the fluid from the sample, and the other sample state is chosen to allow fluid to return to the sample.

3. The method of claim 1,
    wherein the sample fluid state alternations are repeated, and the combined beam is detected with the sample detector during each of several cycles of the sample state alternation, where the sample state alternation causes changes in the amount of fluid within the sample.

4. The method of claim 3, wherein two discrete sample fluid states are alternated.

5. The method of claim 3, wherein the sample fluid states are varied between two extreme sample states, wherein in one extreme sample state substantially all fluid is displaced from the sample, and in the other extreme sample state, substantially all of the displaced fluid content is permitted to return to the sample.

6. The method according to claim 1, wherein the sample matrix comprises biologic tissue and the fluid comprises blood.

7. The method according to claim 1, wherein the wavelengths of the wavelength pair have fixed predetermined values.

8. The method according to claim 1, further comprising:
    directing a second beam of radiation onto the sample, the second beam of radiation having a wavelength that is preferentially absorbed by a component of the fluid, the component being significantly less abundant in the sample matrix; and,
    at a detector, detecting a portion of the second beam that is transmitted through or reflected by the sample to obtain the estimate of the amount of fluid within the sample.

9. The method according to claim 1, wherein the estimate of the amount of fluid in the sample is obtained using laser Doppler anemometry.

10. The method according to claim 1, wherein the estimate of the amount of fluid in the sample is obtained by measuring the electrical impedance of the sample.

11. The method according to claim 1, wherein the estimate of the amount of fluid in the sample is obtained using ultrasound.

12. The method according to claim 1, wherein the first sample fluid state is obtained by applying a compression pressure to the sample for a time period of approximately 1 to 100 seconds.

13. The method according to claim 12, wherein the second sample fluid state is obtained by uncompressing the sample, and the output signal of the sample detector is measured and the amount of fluid is estimated within a measurement time period of approximately 0.1 to 10 seconds after the sample is uncompressed.

14. The method of claim 13, wherein the difference in sample thickness between the two sample fluid states is a predetermined constant.

15. The method of claim 13, wherein the difference in sample thickness between the two sample fluid states is proportional to the sample thickness at the first sample fluid state.

16. The method of claim 13, wherein the estimate of fluid content is obtained at multiple occasions during the measurement time period.

17. The method of claim 12, wherein at one of the sample fluid states, the sample is compressed with a predetermined constant force.

18. The method according to claim 1, wherein the sample is part of a human earlobe.

19. The method according to claim 1, wherein the sample is skin between fingers or toes of a subject.

20. The method according to claim 1, wherein the sample is part of a tongue of a subject.

21. The method according to claim 1, wherein the sample is part of a lip of a subject.

22. The method according to claim 1, wherein the sample is part of a nose of a subject.

23. The method according to claim 1, wherein the sample is part of the nasal septum of a subject.

24. The method according to claim 1, wherein the sample is part of a cheek of a subject.

25. A method of non-invasive measurement of a concentration of a target analyte in a fluid within a sample matrix, the method comprising the steps of:
   directing a combined beam of electromagnetic radiation at the sample, the combined beam including at least two repetitive periods of radiation having different wavelengths, the target analyte having different absorption coefficients for two of the different wavelengths, the two wavelengths forming a wavelength pair;
   while the sample is at a first sample fluid state having an initial amount of fluid, detecting the combined beam with a sample detector arranged to detect a portion of the radiation transmitted through or reflected by the sample to generate an output signal proportional to the intensity of the combined beam at each of the two repetitive periods of radiation of the wavelength pair;
   subjecting the sample to a second sample fluid state to change the amount of fluid within the sample;
   measuring the output signal of the sample detector and obtaining an estimate of the amount of fluid in the sample while the amount of fluid in the sample varies from the initial amount in the first fluid state to a second amount in the second fluid state; and
   combining the measured output signal from the sample detector with the estimate of the amount of the fluid containing the target analyte to produce an estimate of the concentration of the analyte in the fluid, wherein the wavelengths of the wavelength pair are selected to minimize the detected transmission or reflection difference between the wavelength periods measured during a sample state.

26. A method of non-invasive measurement of a concentration of a target analyte in a fluid within a sample matrix, the method comprising the steps of:
   directing a combined beam of electromagnetic radiation at the sample, the combined beam including at least two repetitive periods of radiation having different wavelengths, the target analyte having different absorption coefficients for two of the different wavelengths, the two wavelengths forming a wavelength pair;
   while the sample is at a first sample fluid state having an initial amount of fluid, detecting the combined beam with a sample detector arranged to detect a portion of the radiation transmitted through or reflected by the sample to generate an output signal proportional to the intensity of the combined beam at each of the two repetitive periods of radiation of the wavelength pair;
   subjecting the sample to a second sample fluid state to change the amount of fluid within the sample;
   measuring the output signal of the sample detector and obtaining an estimate of the amount of fluid in the sample while the amount of fluid in the sample varies from the initial amount in the first fluid state to a second amount in the second fluid state; and
   combining the measured output signal from the sample detector with the estimate of the amount of the fluid containing the target analyte to produce an estimate of the concentration of the analyte in the fluid, wherein the intensities of the periods of radiation are adjusted when the sample is at a first sample fluid state, and at least one of the wavelengths of the at least two repetitive periods of radiation is selected to minimize the detected transmission or reflection difference when the sample is at a state different from the first state.

27. The method of claim 26, wherein at the second sample fluid state the amount of fluid within the sample is larger than the amount of fluid in the sample at the first sample state.

28. A method of non-invasive measurement of a concentration of a target analyte in a fluid within a sample matrix, the method comprising the steps of:
   directing a combined beam of electromagnetic radiation at the sample, the combined beam including at least two repetitive periods of radiation having different wavelengths, the target analyte having different absorption coefficients for two of the different wavelengths, the two wavelengths forming a wavelength pair;
   while the sample is at a first sample fluid state having an initial amount of fluid, detecting the combined beam with a sample detector arranged to detect a portion of the radiation transmitted through or reflected by the sample to generate an output signal proportional to the intensity of the combined beam at each of the two repetitive periods of radiation of the wavelength pair;
   subjecting the sample to a second sample fluid state to change the amount of fluid within the sample;
   measuring the output signal of the sample detector and obtaining an estimate of the amount of fluid in the sample while the amount of fluid in the sample varies from the initial amount in the first fluid state to a second amount in the second fluid state; and
   combining the measured output signal from the sample detector with the estimate of the amount of the fluid containing the target analyte to produce an estimate of the concentration of the analyte in the fluid, wherein the start of a sample fluid state variation is synchronized to a pulsation of the sample fluid.

29. The method of claim 28, wherein there is a variable delay between the phase of the pulsation of the fluid and the start of the sample fluid state change.

30. The method of claim 29, wherein the delay is arranged to promote the largest rate of change of fluid content in the sample between the first and second sample fluid states.

31. The method of claim 28, further comprising:
directing a beam of radiation onto the sample, the beam of radiation having a wavelength that is preferentially absorbed by a component of the fluid, this component being significantly less abundant in the rest of the sample; and
at a detector, detecting a portion of the beam that is transmitted through or reflected by the sample to enable synchronization of the start of a change of the sample fluid state to the pulsation of the fluid.

32. The method of claim 28, wherein the synchronization is obtained using a pulse oximeter.

33. The method according to claim 28, wherein the target analyte is glucose, the fluid containing the target analyte is blood, and the pulsations of the fluid containing the analyte are blood pressure variations due to the pumping action of the heart.

34. The method of claim 33, wherein the wavelength that is strongly absorbed by glucose is substantially in the range of 1550 to 1700 nm, and the wavelength lightly absorbed by glucose is substantially in the range of 1350 to 1430 nm.

35. An apparatus for non-invasively measuring a concentration of a target analyte in a fluid within a sample, comprising:
a source for generating a combined beam of electromagnetic radiation including at least two repetitive periods of radiation having different wavelengths, at least two of the wavelengths having different absorption coefficients for the target analyte;
a mount for positioning a sample within an optical path of the combined beam;
means for controlling the amount of fluid within the sample to maintain a first sample fluid state with an initial amount of fluid within the sample, followed by a second sample fluid state with a second amount of fluid within the sample;
a sample detector arranged to detect a portion of the combined beam transmitted through or reflected by the sample, the sample detector generating an output signal proportional to the detected intensity of the combined beam at each of the two repetitive periods of radiation;
means for obtaining an estimate of the amount of the fluid in the sample while the amount of fluid in the sample varies from the initial amount in the first fluid state to a second amount in the second fluid state;
a processor for controlling the measurement sequence and combining the measured output signal from the sample detector with the estimate of the amount of fluid, to produce an estimate of the concentration of the target analyte in the fluid; and
means for measuring a phase of pulsation of the fluid within the matrix.

36. The apparatus of claim 35, wherein the means for measuring a phase of pulsation comprises:
a source for directing radiation at the sample, the radiation having a wavelength that is preferentially absorbed by a component of the fluid, the component being significantly less abundant in the rest of the sample; and
a detector for monitoring the radiation transmitted through or reflected by the sample.

37. The apparatus of claim 36, wherein the sample comprises body tissue, the fluid comprises blood, the pulsations of the fluid comprise blood pressure variations due to the pumping action of the heart, and the component of the fluid comprises hemoglobin.

38. The apparatus of claim 35, wherein the wavelengths of the at least two repetitive periods of radiation have fixed predetermined values.

39. The apparatus of claim 35 wherein the means for obtaining the estimate of the amount of fluid containing the target analyte comprises:
a source for directing radiation at the sample, the radiation having a wavelength that is preferentially absorbed by a component of the fluid, this component being significantly less abundant in the fixed sample matrix; and
a detector for monitoring the radiation transmitted through or reflected by the sample.

40. The apparatus of claim 35 wherein the means for obtaining an estimate of the amount of the fluid comprises a laser Doppler anemometry flow-meter.

41. The apparatus of claim 35 wherein the means for controlling the amount of the fluid in the sample comprises a compression mechanism for compressing and uncompressing the sample.

42. The apparatus of claim 41, wherein the compression mechanism subjects the sample to the first sample fluid state by compressing the sample with a predetermined constant force.

43. The apparatus of claim 41, wherein the compression mechanism is adapted to compress an earlobe of a human patient.

44. The apparatus of claim 41, wherein the compression mechanism is adapted to compress skin between the fingers or toes of a subject.

45. The apparatus of claim 41, wherein the compression mechanism is adapted to compress a tongue of a subject.

46. The apparatus of claim 41, wherein the compression mechanism is adapted to compress a lip of a subject.

47. The apparatus of claim 41, wherein the compression mechanism is adapted to compress a nose of a subject.

48. The apparatus of claim 41, wherein the compression mechanism is adapted to compress the nasal septum of a subject.

49. The apparatus of claim 41, wherein the compression mechanism is adapted to compress a cheek of a subject.

50. The apparatus of claim 41, wherein the compressing force is provided by an electrical actuator.

51. The method of claim 41, wherein the compression force is provided by a hydraulic actuator.

52. The method of claim 41, wherein the compression force is provided by a pneumatic actuator.

53. The apparatus of claim 35 wherein the source for generating a combined begin comprises an incandescent lamp for generating electromagnetic radiation and an acousto-optical tunable filter for producing a radiation beam of at least two repetitive periods having different wavelengths.

54. The apparatus of claim 35 wherein the source for generating a combined beam comprises of at least one laser source for generating at least two repetitive periods of electromagnetic radiation having different wavelengths.

55. The apparatus of claim 35 wherein the source for generating a combined beam comprises of an incandescent lamp for generating electromagnetic radiation and at least one filter for separating the radiation into at least two repetitive periods having different wavelengths.

56. The apparatus of claim 35 wherein the target analyte is glucose.

57. The apparatus of claim 35 wherein one of the repetitive periods of radiation has a wavelength substantially in the range of 1550 to 1700 nm and another of the repetitive periods of radiation has a wavelength substantially in the range of 1350 and 1430 nm.

58. An apparatus for non-invasively measuring a concentration of a target analyte in a fluid within a sample, comprising:

a source for generating a combined beam of electromagnetic radiation including at least two repetitive periods of radiation having different wavelengths, at least two of the wavelengths having different absorption coefficients for the target analyte;

a mount for positioning a sample within an optical path of the combined beam;

means for controlling the amount of fluid within the sample to maintain a first sample fluid state with an initial amount of fluid within the sample, followed by a second sample fluid state with a second amount of fluid within the sample;

a sample detector arranged to detect a portion of the combined beam transmitted through or reflected by the sample, the sample detector generating an output signal proportional to the detected intensity of the combined beam at each of the two repetitive periods of radiation;

means for obtaining an estimate of the amount of the fluid in the sample while the amount of fluid in the sample varies from the initial amount in the first fluid state to a second amount in the second fluid state;

a processor for controlling the measurement sequence and combining the measured output signal from the sample detector with the estimate of the amount of fluid, to produce an estimate of the concentration of the target analyte in the fluid; and means for synchronizing the start of a change in sample state to the phase of pulsation of the fluid within the sample.

59. The apparatus of claim 58, wherein the synchronization includes a variable delay between the phase of the pulsation of the fluid and the start of the sample fluid state change.

60. The apparatus of claim 58, wherein the means for synchronizing includes a pulse oximeter.

61. The apparatus of claim 58, wherein the means for synchronizing includes an electrocardiogram detection device.

62. An apparatus for non-invasively measuring a concentration of a target analyte in a fluid within a sample, comprising:

a source for generating a combined beam of electromagnetic radiation including at least two repetitive periods of radiation having different wavelengths, at least two of the wavelengths having different absorption coefficients for the target analyte;

a mount for positioning a sample within an optical path of the combined beam;

means for controlling the amount of fluid within the sample to maintain a first sample fluid state with an initial amount of fluid within the sample, followed by a second sample fluid state with a second amount of fluid within the sample;

a sample detector arranged to detect a portion of the combined beam transmitted through or reflected by the sample, the sample detector generating an output signal proportional to the detected intensity of the combined beam at each of the two repetitive periods of radiation;

means for obtaining an estimate of the amount of the fluid in the sample while the amount of fluid in the sample varies from the initial amount in the first fluid state to a second amount in the second fluid state;

a processor for controlling the measurement sequence and combining the measured output signal from the sample detector with the estimate of the amount of fluid, to produce an estimate of the concentration of the target analyte in the fluid, wherein one of the wavelengths of the at least two repetitive periods of radiation is selected to minimize the intensity of the detected transmission or reflection difference between the wavelength periods in one of the sample states.

63. A system for non-invasive measurement of a concentration of a target analyte in a fluid within a sample matrix, comprising:

an optical bridge measurement device which generates an output signal indicative of the differential optical absorption in the sample between two or more radiation beams having different wavelengths, the target analyte having different absorption coefficients for two of the different wavelengths;

a fluid variation device which varies the amount of fluid within the sample between an initial amount and a second amount;

a fluid content estimation device which generates an output signal indicative of the amount of fluid in the sample; and a measurement device which records the output of the optical bridge device and the output of the fluid content estimation device multiple times while the amount of fluid varies between the initial amount and the second amount.

64. The system of claim 63, wherein the optical bridge measurement device comprises an incandescent lamp for generating electromagnetic radiation and an acousto-optical tunable filter for producing a radiation beam of at least two repetitive periods having different wavelengths.

65. The system of claim 63, wherein the optical bridge measurement device comprises of at least one laser source for generating at least two repetitive periods of electromagnetic radiation having different wavelengths.

66. The system of claim 63, wherein the optical bridge measurement device comprises of an incandescent lamp for generating electromagnetic radiation and at least one filter for separating the radiation into at least two repetitive periods having different wavelengths.

67. The system of claim 63 wherein the target analyte is glucose.

68. The system of claim 63 wherein one of the radiation beams has a wavelength substantially in the range of 1550 to 1700 nm and another of the radiation beams has a wavelength substantially in the range of 1350 and 1430 nm.

69. The system of claim 63, wherein the fluid content estimation device comprises a source for directing radiation at the sample, the radiation having a wavelength that is preferentially absorbed by a component of the fluid, this component being significantly less abundant in the fixed sample matrix; and a detector for monitoring the radiation transmitted through or reflected by the sample.

70. A method for non-invasive measurement of a concentration of a target analyte in a fluid within a sample matrix, comprising:

varying the amount of fluid within the sample between an initial amount and a second amount;

recording the output of an optical bridge measurement device multiple times while the amount of fluid varies between the initial amount and the second amount; and recording an estimate of the fluid content in the sample multiple times while the amount of fluid varies between the initial amount and the second amount.

71. The method of claim 70, wherein the sample matrix comprises biologic tissue and the fluid comprises blood.

72. The method of claim 71, wherein the target analyte comprises glucose.

73. The method of claim 70, wherein the estimate of fluid content is obtained by directing a beam of radiation onto the sample, the beam having a wavelength that is preferentially absorbed by a component of the fluid, the component being significantly less abundant in the sample matrix; and at a detector, detecting a portion of the second beam that is transmitted through or reflected by the sample to obtain the estimate of the amount of fluid within the sample.

74. The method of claim 70, wherein the initial amount of fluid in the sample is obtained by applying a compression pressure to the sample for a time period of approximately 1 to 100 seconds.

75. The method of claim 74, wherein the second amount of fluid in the sample is obtained by uncompressing the sample, and the output of the optical bridge measurement device is recorded and the estimate of fluid content is recorded over a measurement time period of approximately 0.1 to 10 seconds after the sample is uncompressed.

76. The method of claim 74, wherein the sample comprises tissue from at least one of an earlobe, skin between fingers or toes, a tongue, a lip, a nose, and a cheek.

* * * * *